United States Patent
Mao et al.

(10) Patent No.: US 9,510,798 B2
(45) Date of Patent: Dec. 6, 2016

(54) APPARATUS FOR COUNTERBALANCING A ROTATING ARM IN AN IMAGING SYSTEM

(71) Applicant: General Electric Company, Schenectady, NY (US)

(72) Inventors: Ying Mao, Niskayuna, NY (US); Romain Moulin, Buc (FR)

(73) Assignee: General Electric Company, Niskayuna, NY (US)

( * ) Notice: Subject to any disclaimer, the term of this patent is extended or adjusted under 35 U.S.C. 154(b) by 165 days.

(21) Appl. No.: 14/502,333

(22) Filed: Sep. 30, 2014

(65) Prior Publication Data
US 2016/0089093 A1    Mar. 31, 2016

(51) Int. Cl.
*A61B 6/00* (2006.01)
*F16M 11/04* (2006.01)

(52) U.S. Cl.
CPC ............. *A61B 6/4441* (2013.01); *A61B 6/447* (2013.01); *A61B 6/502* (2013.01); *F16M 11/04* (2013.01)

(58) Field of Classification Search
CPC ..... A61B 6/4441; A61B 6/035; A61B 6/4476; A61B 6/447
See application file for complete search history.

(56) References Cited

U.S. PATENT DOCUMENTS

| | | | |
|---|---|---|---|
| 3,902,070 A | 8/1975 | Amor et al. | |
| 4,233,516 A | 11/1980 | Trepte | |
| 4,955,046 A | 9/1990 | Siczek et al. | |
| 4,989,229 A | 1/1991 | Negrelli et al. | |
| 5,050,204 A | 9/1991 | Siczek et al. | |
| 5,388,141 A * | 2/1995 | Hove | A61B 6/502 378/196 |
| 5,448,607 A | 9/1995 | McKenna | |
| 6,142,667 A | 11/2000 | Pattee | |
| 6,979,123 B2 | 12/2005 | Barta et al. | |
| 2010/0329419 A1 | 12/2010 | Blevis | |
| 2012/0219121 A1 | 8/2012 | Simmons et al. | |
| 2012/0224673 A1 | 9/2012 | Barker et al. | |

* cited by examiner

*Primary Examiner* — Hoon Song
(74) *Attorney, Agent, or Firm* — Melissa K. Dobson (57) ABSTRACT

An apparatus for balancing a statically unbalanced system, particularly useful in balancing X-ray and mammography systems having an X-ray source and detector mounted to a rotational arm, includes a spring mechanism which synchronizes the activation of the spring mechanism with the rotation of the arm of the mammography system. The balancing system reduces the amount of torque necessary to rotate the arm and decreases the overall inertia of the system by eliminating the need for counterweights to maintain balance of the system.

20 Claims, 7 Drawing Sheets

APPARATUS FOR COUNTERBALANCING A ROTATING ARM IN AN IMAGING SYSTEM

BACKGROUND

The embodiments described herein relate generally to imaging apparatuses, and more specifically, to an apparatus including at least one of an X-ray source and X-ray detector mounted to a rotational arm.

In a number of clinical applications, imaging apparatus, and more particularly X-ray apparatuses, which include an X-ray source and X-ray detector mounted to a rotational arm are common These systems provide the ability to rotate the X-ray source and detector to varying angles to obtain images without requiring the patient to move. A mammography system, for example, typically comprises an X-ray source, an X-ray detector, a breast support plate, and a breast compression plate. The source and detector are mounted to opposing ends of an arm, such as a C-arm, and the arm is disposed to rotate around the breast support and compression plates. The breast is positioned between the breast support and breast compression plates to hold the breast in place during mammography, and is arranged between the source and the detector on the opposing ends of the C-arm. During mammography, the C-arm is rotated about the breast plates such that images of the breasts are acquired from varying angles.

For construction reasons, and due to the varying weights of the components, the center of mass of the rotatable C-arm is typically spaced apart from the axis of rotation, and is therefore "unbalanced" about the axis of lateral rotation. In an unbalanced system, a significant torque must be applied to rotate the arm to a desired position. It is desirable, however, to reduce the amount of force required to rotate the arm, to simplify use of the equipment for medical personnel.

Current systems used to reduce the amount of force required to rotate the arm include counterbalance mechanisms. These counterbalance mechanisms used in mammography systems balance the gravitational torque of the rotating arm only partially, leading to much higher power requirement of the actuation system (motor, gear, etc.).

One example of an apparatus and method used to balance the system includes counterweights. The counterweights provide a counteractive torsional force. While counterweights significantly reduce the torsional force that must be applied when rotating the arm, they add significantly to both the weight and cost of the system. Furthermore, the counterweights make it very difficult to move the mammography system from place to place when desired.

Another example of an apparatus and method used to balance the system includes the use of a gas spring. The gas spring is used to counterbalance the arm through a gear set. Such a mechanism may only partially balance the arm. It is estimated that 90% of the motor power of the system is used to compensate for the unbalanced gravitational load. In addition, it is estimated that the gas spring force can degrade up to 20% over its lifespan and has very limited cycle life. Accordingly, the use of a gas spring limits the fatigue life of the system and increases the need for service.

As a result, it is desirable to provide alternate systems and methods for balancing a mammography or other imaging systems comprising an arm in which the torsional force required for rotation is reduced.

BRIEF DESCRIPTION OF THE DISCLOSURE

Aspects and advantages of the disclosure are set forth below in the following description, or may be obvious from the description, or may be learned through practice of the disclosure.

In one aspect, an imaging apparatus is provided. The imaging apparatus includes a base support, an arm rotatably coupled to a rotating component, an imaging component coupled to an end of the arm and a balancing system to balance a torque of the arm. The rotating component is coupled to the base support at a pivot point to provide rotation of the arm about an axis of rotation. The imaging component defines a body having a mass "m". The balancing includes a spring mechanism having a spring rate "k" coupled to the base support and an active connection point via a geometric constraining point. The active connection point is located between the pivot point of the arm and the body and at a distance "d" from the pivot point. The geometric constraining point is located a distance "h" from the pivot point. As the arm is rotated a force applied by the spring mechanism balances a gravitational torque of the arm to provide f=kX, where f is the force of the spring and x is a distance between the active connection point and the geometric constraining point.

In another aspect, an x-ray apparatus is provided. The X-ray apparatus includes a base support, an arm having a first and a second end, an X-ray component coupled to one of the first and second end of the arm and defining a body having a mass "m", a rotating component pivotally coupled to the base support to provide rotation of the arm at a pivot point about an axis of rotation and a balancing system to balance a torque of the arm. The balancing system includes a spring mechanism coupled to the base support at an inactive connection point and to an active connection point via a geometric constraining point. The active connection point is located between the pivot point of the arm and the mass and at a distance "d" from the pivot point. The geometric constraining point is located a distance "h" from the pivot point. The apparatus further including an extender arm configured parallel to the arm and mounted to the rotating component for rotation relative to the base support and a cable guide system configured to support movement of a cable drive mechanism. The cable drive mechanism is coupled at a first end to a second end of the spring mechanism and coupled at a second end to an active connection point on the extender arm. As the arm is rotated the balancing system maintains the same order of magnitude of an angle of rotation of the arm and an angle of rotation of the extender arm. Furthermore, as the arm is rotated a force applied by the spring mechanism balances a gravitational torque of the arm to provide f=kX, where f is the force of the spring, k is a spring rate of the spring mechanism and x is a distance between the active connection point and the geometric constraining point.

In yet another aspect, a mammography system is provided. The mammography system including a base support, an arm coupled to a rotating component for rotating a body having a mass "m" relative to the base support about an axis of rotation, an extender arm configured parallel to the arm and coupled to the rotating component for rotating relative to the base support about the axis of rotation and a balancing system. The rotating component is coupled to the base support. The balancing system includes a spring mechanism coupled to the base support and to an active connection point located on the extender arm between the axis of rotation of the arm and the body via a geometric constraining point. The active connection point is located a distance "d" from the pivot point. The geometric constraining point is located a distance "h" from the pivot point. As the arm is rotated about the axis of rotation, the balancing system synchronizes the angle of rotation of the arm with the angle of rotation of the extender arm such that the applied force of the spring mechanism counteracts the torque force of the arm to statically balance the system and provide f=kX, where f is the force of the spring, k is a spring rate of the spring mechanism and x is a distance between the active connection point and the geometric constraining point.

BRIEF DESCRIPTION OF THE DRAWINGS

A full and enabling disclosure of the present disclosure, including the best mode thereof to one skilled in the art, is set forth more particularly in the remainder of the specification, including reference to the accompanying figures, in which.

Corresponding reference characters indicate corresponding parts throughout the several views of the drawings.

DETAILED DESCRIPTION OF THE DISCLOSURE

The exemplary methods and systems described herein overcome the structural disadvantages of known imaging systems by providing a balancing system that reduces the torque required for rotation of arm having mounted thereto at least one of an X-ray source or an X-ray detector. Each example is provided by way of explanation of the disclosure, not limitation of the disclosure. In fact, it will be apparent to those skilled in the art that modifications and variations can be made in the present disclosure without departing from the scope or spirit thereof. For instance, features illustrated or described as part of one embodiment may be used on another embodiment to yield a still further embodiment. Thus, it is intended that the present disclosure covers such modifications and variations as come within the scope of the appended claims and their equivalents. Although exemplary embodiments of the present disclosure will be described generally in the context of a mammography system for purposes of illustration, one of ordinary skill in the art will readily appreciate that embodiments of the present disclosure may be applied to any imaging system utilizing a rotating arm, and not limited to mammography systems.

Figure 1:
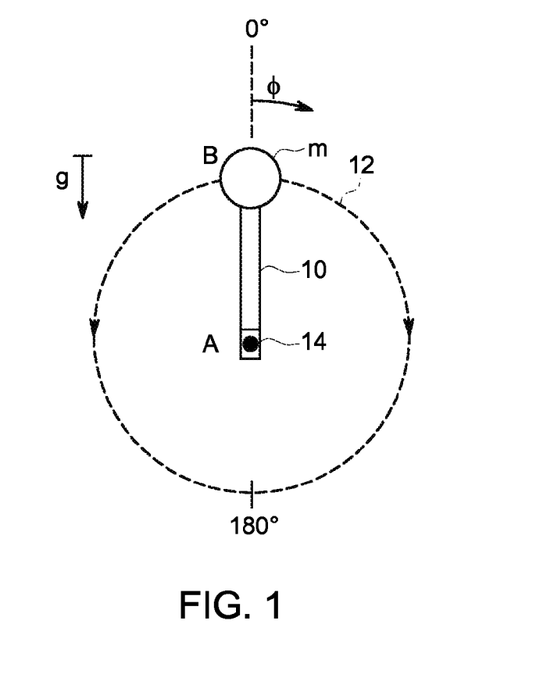
FIG. 1 is a block diagram of a mass mounted to a rotatable arm.

Referring now to the drawings, wherein identical numerals indicate the same elements throughout the figures, FIG. 1 provides an arm 10 having a length AB and comprising a rotating body 12 having mass "m", and a center of mass "B", rotatable about an axis of rotation 14 or pivot point "A". When the arm 10 is released from a static position, the arm rotates around the rotation of axis 14 in a direction determined by the force of gravity "g" the arm reaches a stable position when the direction of the arm 10 correlates with the direction of the gravity vector "g", and therefore when the angle of rotation is either zero or one hundred and eighty degrees. When released from a stable position, as shown, at which the angle of rotation is Φ=0°, the direction of motion of the arm around the axis 14 is downward, and as required by the principle of minimum potential, stabilizes at the angle Φ=180°. As the arm rotates, the torque of the arm ($M_A(\Phi)$) at a given rotational angle on axis 14 is defined by the following equation:

$$M_A(\Phi) = m*g*AB*\sin \Phi \quad \text{[equation 1]}$$

As described above, the minimum potential stable position for the mass "B" is Φ=180°, with the center of mass directly below the axis of rotation 14. To balance the system to maintain the unbalanced body in a static position which is not equivalent to 180 degrees, an opposing torque must be applied to counter the torque "$M_A(\Phi)$" of the center of mass "B".

Figure 2:
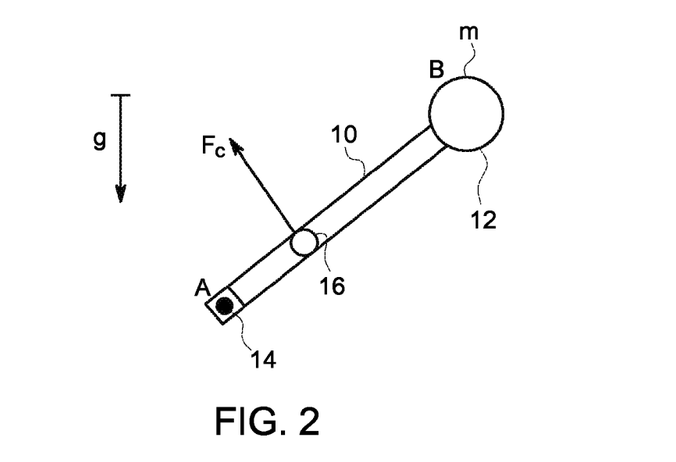
FIG. 2 is a block diagram of a counteractive force for balancing the system of FIG. 1.

Referring now to FIG. 2, to provide a counteractive torque, a mechanism which is rotatable about the minimum potential static resting point (i.e. the one hundred and eighty degree resting point) of the center of mass B and which provides an active force on the arm 10 in a circular path can be provided to deliver a torque in the direction opposite to and of substantially the same magnitude as the torque "$M_A(\Phi)$". Here, the counteractive force is $F_C$, and is perpendicularly directed at an active connection point 16(C) on the arm 10, located a distance AC along the arm 10. Referring again to equation 1, to balance the torque "$M_A(\Phi)$", the counteractive torque must be equivalent to the downward torque of the arm 10. Therefore:

$$m*g*AB*\sin (\Phi) = F_C*AC \quad \text{[equation 2]}$$

The torque $F_C*AC$ provides static balancing, such that properly chosen values of $F_C$ and AC results in a balance in which the sum of the torques in the system $\Sigma MA(\Phi)$ equals zero.

Figure 3:
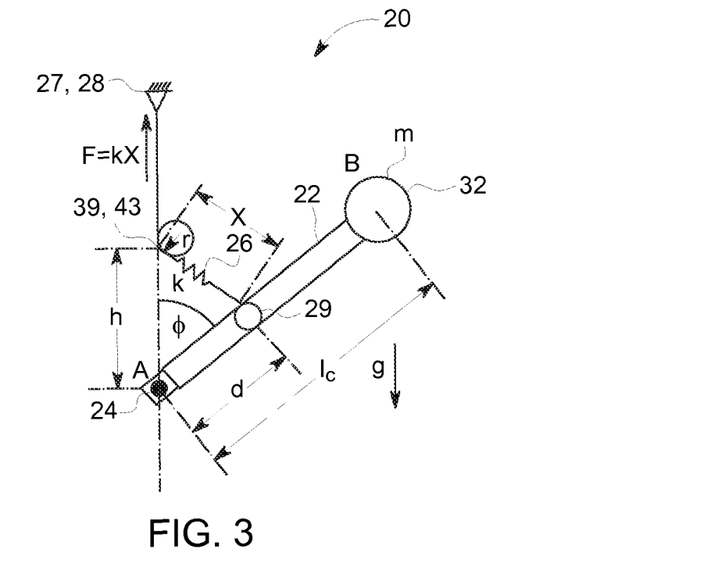
FIG. 3 is a block diagram of a balancing system for balancing a rotatable arm, according to one or more embodiments disclosed herein.
Figure 4:
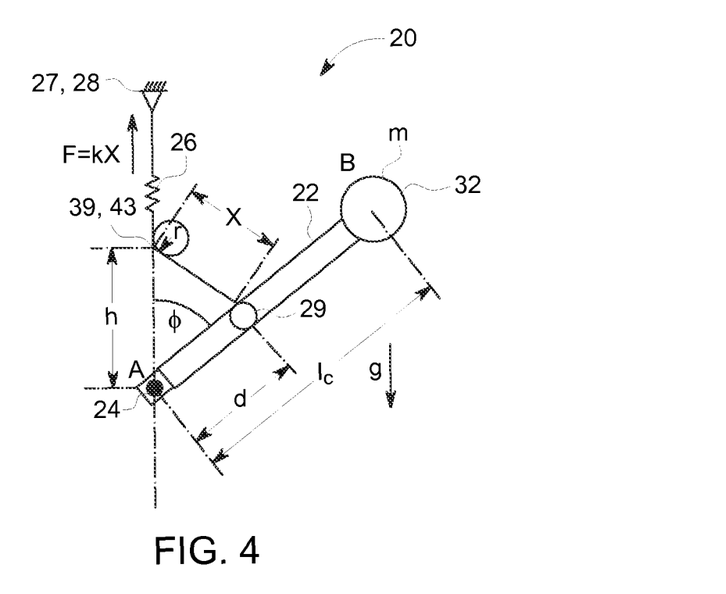
FIG. 4 is a block diagram of a balancing system for balancing a rotatable arm, according to one or more embodiments disclosed herein.
Figure 5:
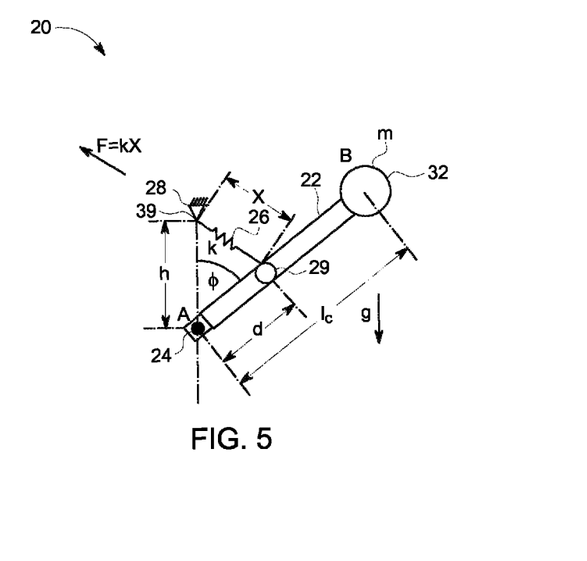
FIG. 5 is a block diagram of a balancing system for balancing a rotatable arm, according to one or more embodiments disclosed herein.

Referring now to FIGS. 3-5, illustrated are block diagrams showing alternate embodiment of a balancing system 20 for providing the opposing torque, described above. In the illustrated embodiments, the balancing system 20 is generally comprised of a serial-chain mechanism on a revolute joint. As illustrated, in each embodiment the balancing system 20 includes an arm 22, generally similar to arm 10 of FIGS. 1 and 2. The arm 22 is configured to pivot around an axis of rotation 24 or pivot point "A", that may also be referred to herein as a revolute joint. The axis of rotation 24 or pivot point "A" is generally similar to pivot point 14 of FIGS. 1 and 2. In the embodiments of FIGS. 3 and 4, a spring mechanism 26 is connected via a pulley like system, described presently, between a mounting anchor 28 at an inactive connection point 27, and the arm 10, with one fixed end on the gantry housing, or the like, at a geometric constraining point 39 a distance "h" from the pivot point 24 and one moving end connected to the arm 22 at an active connection point 29 (effectively, an extension/extender arm configured parallel to the arm 10 may be needed inside the gantry, as described presently) a distance "d" from the pivot point 24. In the embodiment of FIGS. 3 and 4, the geometric constraining point 39 is configured as a cable routing point 43. The fixed end is along gravity direction from the pivot axis. The spring has the following characteristic:

$$F = kX \quad \text{[equation3]}$$

where F=spring force, x=distance between the active connection point 29 and the geometric constraining point 39 and k=spring rate.

The system stays in equilibrium against gravity at any angle without additional torque at the rotary joint. The gravitational torque can be completely counterbalanced. As indicated, in the embodiments of FIGS. 3 and 4, the mechanism 20 comprises the spring mechanism 26 and a cable drive mechanism routed through a cable guide system and connecting the arm 10 and the spring mechanism 26. By such a mechanism 20, f=kX can be achieved.

The relative locations of the geometric constraining point 29, the active connection point 29 and the pivot point 24 are optimally selected to completely balance the gravitational torque of the arm 22 at any angle Φ, or in other words, properly choosing h and d such that Equation 2 is satisfied at any angle Φ. After the spring rate k is chosen, optimal values for h and d are chosen to achieve 100% counterbalance according to the equation:

$$k = mgl_c/hd \quad \text{[equation4]}$$

where k=spring rate, m=mass of rotating body 12, g=gravity, $l_c$=distance between pivot point 24 and rotating body 12, h=distance between pivot point 24 and the geometric constraining point 39 and d=distance between pivot point 24 and the active connection point 29.

There is no change in potential energy in the system if equation 4 is met. A spring mechanism 26 having a spring rate k as stated, provides a system that stays in equilibrium against gravity at any angle without additional torque at the pivot point 24. The gravitational torque can be completely counterbalanced.

The balancing system 20 comprises the spring mechanism 26 coupled between a pivotal or rotational axis, and more particularly the revolute joint 24 and an active connection point 29 on the arm 22, the active connection point 29 being provided between the axis of rotation of the arm 22 and a body 32 of mass "m". The statically unbalanced mass m, with center of gravity "B" is rotatable around the "A" axis 24, due to the force of gravity, as described above, to provide a torque "$M_A(\Phi)$" which, when not in a static position, provides unbalance in the system. The unbalance is dependent on the angle of rotation Φ and is directed to drive the mass "m" to the rotation angle of Φ=180°. As the center of mass "B" rotates on a circular path around the axis 24, the active connection point 29 on the arm 22 also rotates on a circular path, at the same angle, thus the spring mechanism 26 provides a torque nearly equal to, but in a direction opposite the torque of the arm "$M_A(\Phi)$". The spring mechanism 26 is actuated via a cable guide system, described presently, and anchored to an anchor point on the gantry housing.

In yet another alternate embodiment illustrated in FIG. 5, the spring mechanism 26 may be anchored at a first end to the active connection point 29 and at a second end to the geometric constraining point 39. In this particular embodiment, the spring mechanism 26 is coupled to a mounting anchor 28 at an inactive connection point 27, and the arm 10, with one fixed end on the gantry housing, or the like, at a geometric constraining point 39 a distance h from the pivot point 24 and one moving end connected to the arm 22. In the embodiment of FIG. 5, the geometric constraining point 39 is configured as a spring attachment point 44 and thus fixed anchor, and there is no need for the cable guide system as in FIGS. 3 and 4. Corresponding reference characters indicate corresponding parts throughout FIGS. 3-5.

Figure 6:
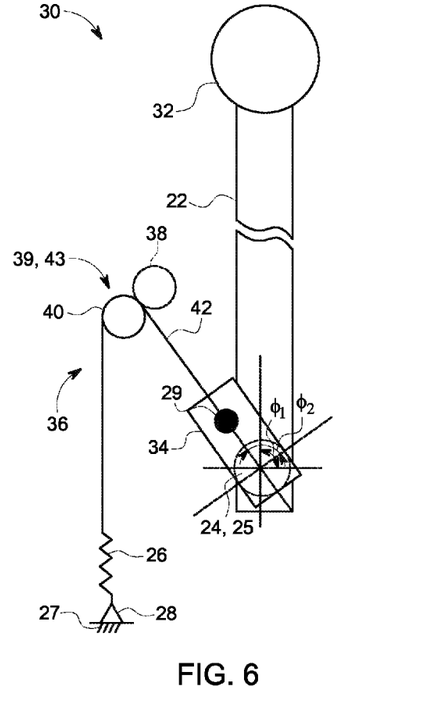
FIG. 6 is a schematic illustration of a balancing system including a spring mechanism and a cable guide system for applying a counteractive torque to the rotatable arm, according to one or more embodiments disclosed herein.
Figure 7:
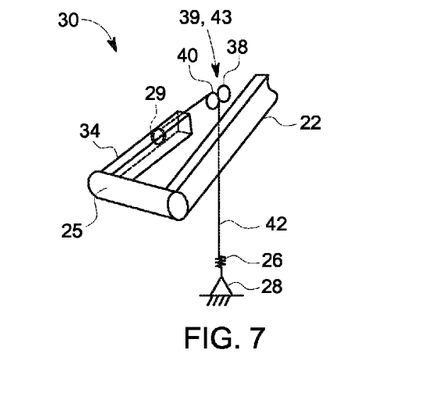
FIG. 7 an isometric schematic illustration of the balancing system of FIG. 6, including a spring mechanism and a cable guide system for applying a counteractive force to the rotatable arm, according to one or more embodiments disclosed herein.

Referring now to FIGS. 6 and 7, illustrated is a balancing system 30, including the spring mechanism 26 and a cable guide system, described presently, for applying a counter-active force to the rotatable arm 22. Again, it is noted that identical numerals indicate the same elements throughout the drawings. In this particular embodiment, the balancing system 30 further includes an extender arm 34 configured parallel to the rotatable arm 22 and coupled to the balanced body 32 via the revolute joint 24, and more particularly a rotating component 25, and the rotatable arm 22. In the illustrated embodiment, the spring mechanism 26 is separated from the active connection point 29 by a cable guide system 36. In an embodiment, the cable guide system 36 comprises a first wheel 38, a second wheel 40, and a cable drive mechanism 42 extending from the active connection point 29 on the extender arm 34 to the spring mechanism 26 via the geometric constraining point 39, and more particularly, the cable routing point 43. In an alternate embodiment, the cable guide system 36, and more the cable routing point 43 may be configured to include a single pulley, a smooth guide pin, a smooth guide ring, or other means of guiding the cable as long as f=kx (as indicated in FIGS. 3-5) is achieved. In an embodiment, the cable guide system 36 is used to guide the cable such that f=kx is maintained over a full rotation.

In an embodiment, the balancing system 30, and more particularly the spring mechanism 26 and the cable guide system 36 are configured to provide rotation of the extender arm 34 and the arm 22, such that the angle of rotation $\Phi_2$ of the extender arm 34 is equal in magnitude to the angle of rotation $\Phi_1$ of the arm 22. Furthermore, the spring mechanism 26 provides a torque nearly equal to but in a direction opposite the torque of the arm "$M_A(\Phi)$", which results in a balancing machine with properties similar to those described above with reference to FIGS. 1-3.

Figure 8:
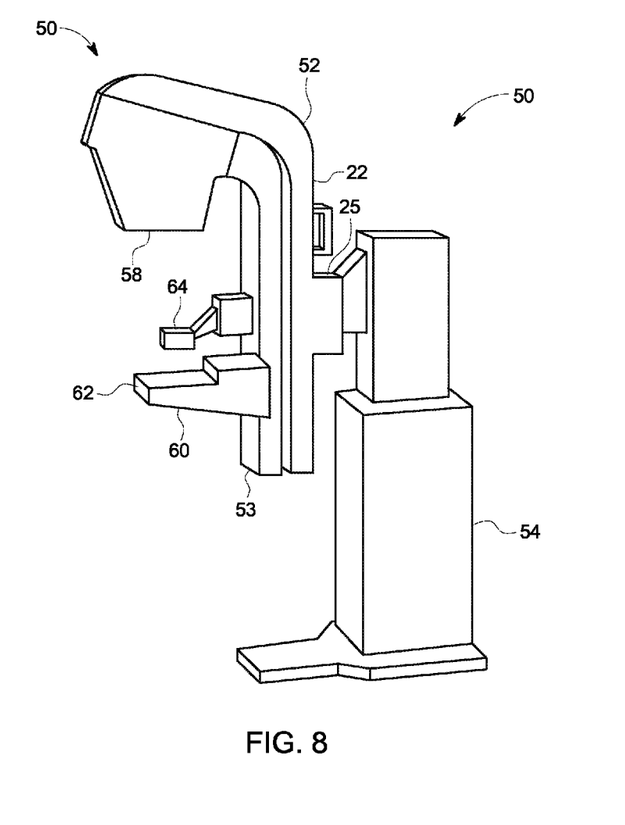
FIG. 8 is an isometric view of a typical mammography system, including a balancing system, according to one or more embodiments disclosed herein.

Referring now to FIG. 8, an X-ray apparatus 50 including a rotatably mounted arm 22 is shown. Here, the X-ray apparatus 50 is a mammography system, comprising the arm 22 rotatably mounted to a base support 54 through a rotating component 25. An X-ray source 58 is coupled to a first end 52 of the arm 22, and an X-ray detector 60 is coupled proximate an opposing end 53 of the arm 22, the X-ray source 58 extending substantially perpendicular to the arm 22 and directed toward the X-ray detector 60, which also extends from the arm 22 such that the detector 60 receives radiation produced by the source 58. A breast support plate 62 and a breast compression plate 64 are positioned between the X-ray source 58 and the X-ray detector 60.

Figure 9:
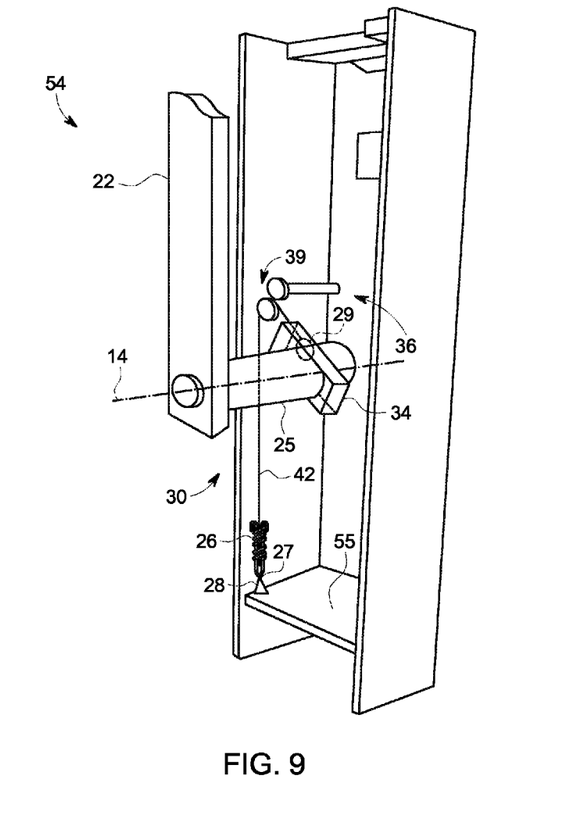
FIG. 9 is a perspective view of a support base for the mammography system of FIG. 8 incorporating a balancing system as described herein with a portion of the housing removed to illustrate the balancing system, according to one or more embodiments disclosed herein.
Figure 10:
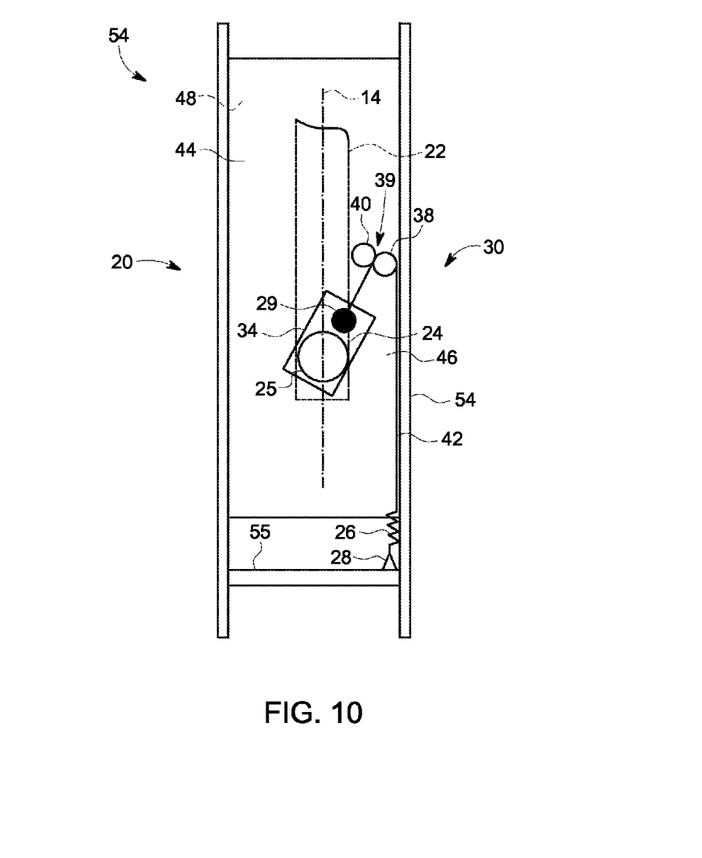
FIG. 10 is an elevation view of a support base for the mammography system of FIG. 8 incorporating an alternate embodiment of a balancing system as described herein with a portion of the housing removed to illustrate the balancing system, according to one or more embodiments disclosed herein.

Referring now to FIGS. 9 and 10, illustrated in an isometric front view and a rear elevation view, respectively, are embodiments of the base support 54 of FIG. 8. FIG. 9 is shown with the front housing removed to provide a view of the balancing system 30. FIG. 10 is shown with the rear housing removed to provide a view of an alternate configuration of the balancing system 30. As best illustrated in FIG. 9, the base support 54 having a front housing removed, has disposed therein the balancing system 30 including the spring mechanism 26 coupled to the cable guide system 36. Here, the cable guide system 36 comprises the first wheel 38 and the second wheel 40 having the cable drive mechanism 42 in alignment therewith, and coupled to the extender arm 34 and the spring mechanism 26. The extender arm 34, controlled by the balancing system 30, is configured to rotate about the same axis of rotation 14 with the arm 22. The spring mechanism 26, is coupled via the cable drive mechanism 42, between the inactive connection point 27, and more particularly at the mounting anchor 28 anchored to a wall 55 of the base support 54, and the active connection point 29 on the extender arm 34 such that the active connection point 29 of the balancing system 30, via the cable drive mechanism 42, rotates with the extender arm 34. The balancing system 30 provides for the opposing torque of the arm 22 to balance the system, and is therefore the spring mechanism 26 is selected to provide a torque nearly equal to, but in a direction opposite, the torque of the arm "$M_A(\Phi)$", as differentiations in the applied force can degrade the efficiency of the balancing. Suitable spring mechanisms 26 include an extension spring, a compression spring, an extension drawbar spring, or similar devices which will be apparent to those of skill in the art.

In an embodiment, the cable guide system 36, and more particularly the first wheel 38 and the second wheel 40 are configured to maintain alignment of the cable drive mechanism 42 and permit movement of cable drive mechanism 42 in response to balancing of the system. Therefore, as the arm 22 is rotated, the spring mechanism 26 is actuated (compression/extension) as a result of rotational movement of the extender arm 34 via the cable drive mechanism 42. Although the first wheel 38 and the second wheel 40 are shown as of the same size, varying ways of configuring the cable guide system 36 will be apparent to those of ordinary skill in the art.

Similar to the embodiment of FIG. 9, as previously indicated FIG. 10 illustrates in an elevation view, the rear housing of the base support 54 removed to provide a view of an alternate configuration of the balancing system 30. As best illustrated in FIG. 10 the base support 54 having the rear housing removed, has disposed therein the balancing system 30 including the spring mechanism 26 coupled to the cable guide system 36 and the extender arm 34. As previously described, the cable guide system 36 comprises the first wheel 38 and the second wheel 40 having the cable drive mechanism 42 in alignment therewith, and coupled at the active connection point 29 to the extender arm 34 and the spring mechanism 26. In contrast to the previously described embodiment of FIG. 9, in this particular embodiment, the balance system 30, including the cable guide system 36, extender arm 34 and the spring mechanism 26 are configured on a first side 44 of a vertical wall member 46 and the arm 22 (as indicated by dashed line) is cooperatively configured on an opposed second side 48 of the vertical wall member 46. The rotating component 25 provides cooperative engagement of the extender arm 34 and the rotatable arm 22 through the vertical wall member 26. The vertical wall member 46 provides operable separation of the balancing system 30 and the arm 22. In an embodiment, the vertical wall member 46 may be the front housing of the base support 54.

The arm 22, controlled by the balancing system 30, is configured to rotate about the same axis of rotation 14 as the extender arm 34. The spring mechanism 26, is coupled via the cable drive mechanism 42, between the mounting anchor 28 anchored to the wall 55 of the base support 54, and the active connection point 29 on the extender arm 34 such that the active connection point 29 of the balancing system 26, rotates with the extender arm 34. The balancing system 30 provides for the opposing torque of the arm 22 to balance the system, and is therefore the spring mechanism 26 is selected to provide a torque nearly equal to, but in a direction opposite, the torque of the arm "$M_A(\Phi)$", as differentiations in the applied force can degrade the efficiency of the balancing. As previously indicated with regard to the embodiment of FIG. 9, suitable spring mechanisms 26 include an extension spring, a compression spring, an extension drawbar spring, or similar devices which will be apparent to those of skill in the art.

Similar to the previous embodiment, the cable guide system 36, and more particularly the first wheel 38 and the second wheel 40 are configured to maintain alignment of the cable drive mechanism 42 and ultimately permit movement of the arm 22 in response to balancing of the system. Therefore, as the arm 22 is rotated, the spring mechanism 26 is actuated (compression/extension) as a result of rotational movement of the extender arm 34 via the cable drive mechanism 42.

In operation, initial images are acquired by the system 50 with the arm 22 in the zero degree position, as best illustrated in FIG. 8. After images are acquired in this position, the clinician conducting the test typically rotates the arm 22 to a ninety degree position for additional image acquisition. As the arm 22 is rotated, the extender arm 34 is caused to rotate via the rotating component 25 and the cable drive mechanism 42. This rotational movement causes actuation of the spring mechanism 26 providing a counteractive torque of the arm 22. The counteractive torque is selected to balance the system such that the amount of force required to rotate the arm 22 is significantly reduced. Furthermore, the balancing system 30 eliminates the need for heavy counterweights, also reducing the overall weight of the X-ray system significantly.

Accordingly, as disclosed herein and as illustrated in FIGS. 1-10, provided are various technological advantages and/or improvements over existing counterbalancing system. The proposed counterbalance mechanism as disclosed herein has the potential to reduce power requirement of the imaging system actuation system by approximately 80%, which may lead to a significant cost reduction in the actuation system. The system parameters may be further optimized and adjusted for less uncompensated torque, a higher reduction in motor power. Specifically, adjustment of the distance "h", the distance "d" and the spring rate k may be made to optimize for least uncompensated torque given variations in the system components (spring rate, etc.) and assembly tolerances. Implementation of the proposed counterbalance mechanism is feasible for use in the gantry of known mammography imaging systems.

The proposed counterbalance mechanism drastically reduces unbalanced gravitational loads exerted upon the arm of the disclosed imaging system. The mechanism uses a spring, such as a coil spring, configured in a manner that theoretically balances all of the static load of the arm at any arm angular position. As a result, load capacity of the actuation system can be greatly reduced, which reduces the system initial carrying value (ICV). The spring mechanism may be fabricated according to conventional methods at low cost. Performance of the spring mechanism is robust against design parameter variations. In comparison with known cogwheel/gas spring counterbalance systems, the proposed balancing system advantageously reduces static counterbalance torque by approximately 80%, while minimizing deterioration of the spring mechanism with repeated use, thereby increasing the life expectancy of the balancing system.

Exemplary embodiments of a balancing system are described in detail above. Although the balancing system has been described with reference to an X-ray source and detector, the balancing system as described above can be used in any unbalanced system, including other types of imaging apparatuses, and particularly those in which a source and detector are provided on opposite ends of a rotatable arm. Other applications will be apparent to those of skill in the art. Accordingly, the balancing system is not limited to use with the specified mammography system described herein. Moreover, the present disclosure is not limited to the embodiments of the balancing system described in detail above. Rather, other variations of the balancing system embodiments may be utilized within the spirit and scope of the claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

While there has been shown and described what are at present considered the preferred embodiments of the disclosure, it will be obvious to those skilled in the art that various changes and modifications can be made therein without departing from the scope of the disclosure defined by the appended claims.

What is claimed is:

1. An imaging apparatus, comprising:
   a base support;
   an arm rotatably coupled to a rotating component, the rotating component coupled to the base support at a pivot point to provide rotation of the arm about an axis of rotation;
   an imaging component coupled to an end of the arm and defining a body having a mass "m"; and
   a balancing system to balance a torque of the arm, the balancing system comprising:
      a spring mechanism having a spring rate "k" coupled to the base support and an active connection point via a geometric constraining point, the active connection point located between the pivot point of the arm and the body and at a distance "d" from the pivot point, the geometric constraining point located a distance "h" from the pivot point; and
      a cable guide system configured to support movement of a cable drive mechanism, the cable drive mechanism coupled at a first end to a second end of the spring mechanism and coupled at a second end to the active connection point,
   wherein as the arm is rotated a force applied by the spring mechanism balances a gravitational torque of the arm to provide f=kX, where f is the force of the spring and x is a distance between the active connection point and the geometric constraining point.

2. The imaging apparatus as defined in claim 1, wherein the spring mechanism provides a torque substantially equal to and in an opposite direction of the gravitational torque of rotating arm.

3. The imaging apparatus as defined in claim 1, wherein as the arm is rotated a force applied by the spring mechanism balances the gravitational torque of the arm to provide $k=mgl_c/hd$, where m is a mass of the body, g is a gravitational force and $l_c$ is a distance between the pivot point and the body.

4. The imaging apparatus as defined in claim 1, wherein the cable guide system further comprises a first wheel and a second wheel configured to support movement of a cable drive mechanism.

5. The imaging apparatus as defined in claim 1, wherein the geometric constraining point is configured as one of a cable routing point or a spring attachment point.

6. The imaging apparatus as defined in claim 1, wherein the spring mechanism comprises a coil spring.

7. The imaging apparatus as defined in claim 1, further comprising an extender arm configured in synchronous motion with the arm.

8. The imaging apparatus as defined in claim 1, wherein the balancing system is disposed within the base support of the X-ray apparatus.

9. An X-ray apparatus, comprising:
   a base support;
   an arm having a first and a second end, an X-ray component coupled to one of the first and second end of the arm and defining a body having a mass "m";
   a rotating component pivotally coupled to the base support to provide rotation of the arm at a pivot point about an axis of rotation; and
   a balancing system to balance a torque of the arm, the balancing system comprising:
      a spring mechanism coupled to the base support at an inactive connection point and to an active connection point via a geometric constraining point, the active connection point located between the pivot point of the arm and the body and at a distance "d" from the pivot point, the geometric constraining point located a distance "h" from the pivot point,
      an extender arm configured parallel to the arm and mounted to the rotating component for rotation relative to the base support; and
      a cable guide system configured to support movement of a cable drive mechanism, the cable drive mechanism coupled at a first end to a second end of the spring mechanism and coupled at a second end to the active connection point on the extender arm,
   wherein as the arm is rotated the balancing system maintains the same order of magnitude of an angle of rotation of the arm and an angle of rotation of the extender arm, and
   wherein as the arm is rotated a force applied by the spring mechanism balances a gravitational torque of the arm to provide f=kX, where f is the force of the spring, k is a spring rate of the spring mechanism and x is a distance between the active connection point and the geometric constraining point.

10. The X-ray apparatus as defined in claim 9, wherein as the arm is rotated a force applied by the spring mechanism balances a torque of the arm to provide $k=mgl_c/hd$, where k is a spring rate of the spring mechanism, g is gravity, and $l_c$ is a distance between the pivot point and the body.

11. The X-ray apparatus as defined in claim 9, wherein the spring mechanism comprises a coil spring comprising one of an extension spring, a compression spring, or an extension drawbar spring.

12. The X-ray apparatus as defined in claim 9, wherein the arm, the rotating component and the extender arm rotate about a single axis of rotation.

13. The X-ray apparatus as defined in claim 9, wherein the balancing system is disposed within the base support of the X-ray apparatus.

14. The X-ray apparatus as defined in claim 13, wherein the balancing apparatus and the arm are configured on opposed sides of a vertical wall structure of the base support.

15. The X-ray apparatus as defined in Claim 9, wherein the apparatus is a mammography system.

16. A mammography system, comprising:
a base support;
an arm coupled to a rotating component for rotating a body having a mass "m" about a pivot point relative to the base support about an axis of rotation, the rotating component coupled to the base support;
an extender arm configured parallel to the arm and coupled to the rotating component for rotating relative to the base support about the axis of rotation; and
a balancing system comprising:
a spring mechanism coupled to the base support and to an active connection point located on the extender arm between the axis of rotation of the arm and the body via a geometric constraining point, the active connection point located a distance "d" from the pivot point, the geometric constraining point located a distance "h" from the pivot point; and
a cable guide system configured to support movement of a cable drive mechanism, the cable drive mechanism coupled at a first end to a second end of the spring mechanism and coupled at a second end to the active connection point,
wherein as the arm is rotated about the axis of rotation, the balancing system synchronizes the angle of rotation of the arm with the angle of rotation of the extender arm such that the applied force of the spring mechanism counteracts the torque force of the arm to statically balance the system and provide f=kX, where f is the force of the spring, k is a spring rate of the spring mechanism and x is a distance between the active connection point and the geometric constraining point.

17. The mammography system of claim 16, wherein as the arm is rotated a force applied by the spring mechanism balances the gravitational torque of the arm to provide $k=mgl_c/hd$, where g is a gravitational force and $l_c$ is a distance between the axis of rotation and the body.

18. The mammography system of claim 16, wherein the spring mechanism comprises a coil spring.

19. The mammography system of claim 16, wherein a torque applied by the balancing system is selected to counteract the torque generated by the arm.

20. The mammography system of claim 16, wherein the balancing system is disposed within a base support of the X-ray apparatus.

* * * * *